United States Patent

Didier et al.

Patent Number: 5,273,549
Date of Patent: Dec. 28, 1993

[54] ALKANEPOLYCARBOXYLIC ACID DERIVATIVES AS CROSS-LINKING AGENTS OF CELLULOSE, NEW DERIVATIVES AND TEXTILE FINISHES

[75] Inventors: Wilhelm Didier, Issy Les Moulineaux; Fietier Isabelle, Choisy Le Roi, both of France

[73] Assignee: Societe Francaise Hoechst, Puteaux, France

[21] Appl. No.: 785,117

[22] Filed: Oct. 30, 1991

[30] Foreign Application Priority Data

Oct. 30, 1990 [FR] France .................. 9013456

[51] Int. Cl.$^5$ .................. D06M 11/68
[52] U.S. Cl. .................. 8/127.1; 8/116.1; 8/120
[58] Field of Search .................. 8/127.1

[56] References Cited

U.S. PATENT DOCUMENTS

| | | | |
|---|---|---|---|
| 3,300,337 | 1/1967 | Cooper | 428/389 |
| 3,923,876 | 12/1975 | Heins et al. | 260/502.4 |
| 4,820,307 | 4/1989 | Welch et al. | 8/120 |
| 4,936,865 | 6/1990 | Welch et al. | 8/120 |
| 5,042,986 | 7/1991 | Kitchens et al. | 8/120 |

FOREIGN PATENT DOCUMENTS 2180101 11/1973 France .

*Primary Examiner*—Asok Pal
*Assistant Examiner*—P. Achutamurthy
*Attorney, Agent, or Firm*—Browdy and Neimark

[57] ABSTRACT

Use as cellulose cross-linking agents of derivatives of alkanepolycarboxylic acids corresponding to general formula I:

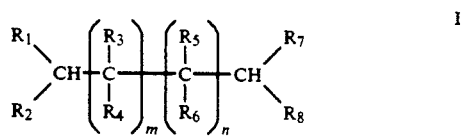

in which:

n, m = 0 or 1, $R_1$, $R_3$, $R_5$ and $R_7$ = H or COOH it being understood that at least two of the substituents from the said substituents $R_1$, $R_3$, $R_5$ and $R_7$ represent a carboxyl group, $R_2$, $R_4$, $R_6$, $R_8$ = H or PO(OH)(OR) where R = H or Alk $C_1$–$C_4$, it being understood that only one substituent from the said substituents $R_2$, $R_4$, $R_6$ and $R_8$ represents said PO(OH)(OR) group, textile finishes containing said products of formula I and new derivatives of formula I.

19 Claims, No Drawings

ALKANEPOLYCARBOXYLIC ACID DERIVATIVES AS CROSS-LINKING AGENTS OF CELLULOSE, NEW DERIVATIVES AND TEXTILE FINISHES

The present relates to the use of alkanepolycarboxylic acid derivatives as cross-linking agents of cellulose, new derivatives and textile finishes.

The cross-linking agents of cellulose most commonly used to impart crease-resistant properties to cellulose fabric are formaldehyde addition products with various amides such as urea, 4-5-dihydroxy ethyleneurea, ethyleneurea, optionally esterified with methanol to the state of N-methylol or N-methylolamide derivatives such as 1,3-dimethylol-4,5-dihydroxy ethyleneurea (DMDHEU). However, these finishes release formaldehyde not only during their application on the cellulose fabrics but also during storage and use of these fabrics. In an attempt to remedy this disadvantage, it is proposed to cross-link the cellulose with, either free or salified polycarboxylic acids, optionally in the presence of a cross-linking catalyst chosen from the group constituted by alkali metal salts of phosphinic, phosphonic, phosphoric or polyphosphoric acids (Gagliardi and Shippee, American dyestuff reporter, 52, p. 300–p. 303, (1963) and Rowland et al, Textile Research Journal, 37, 933–941, (1967), 38, 634–643, (1968), U.S. Pat. Nos. 3,526,048 and 4,820,307), or polyphosphonic acids in the presence of cyanamide (J. TURNER, Text. Res. J., 49, 244, (1979)). However, these cross-linking agents are not entirely satisfactory, some are expensive and not very soluble in water, others provide finishes which are easily removed with domestic washing.

In order to remedy these disadvantages, the applicant has discovered with astonishment that alkanepolycarboxylic acid derivatives were remarkable cross-linking agents of cellulose giving the cellulose fabric excellent crease-resistant properties combined with good durability with washing, without altering the colours.

This is why a subject of the present invention is the use as a cross-linking agent of cellulose of alkanepolycarboxylic acid derivatives corresponding to general formula I:

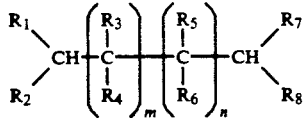

in which:

n and m, identical or different, are equal to 0 or 1, $R_1$, $R_3$, $R_5$ and $R_7$ represent a hydrogen atom or a carboxyl group, it being understood that at least two substituents from the said substituents $R_1$, $R_3$, $R_5$ and $R_7$ represent a carboxyl group, $R_2$, $R_4$, $R_6$ and $R_8$ represent a hydrogen atom or a -PO(OH)(OR) group where R is a hydrogen atom or a $C_1$-$C_4$ alkyl group, it being understood that only one substituent from the said substituents $R_2$, $R_4$, $R_6$ and $R_8$ represents said -PO(OH)(OR) group.

The $C_1$-$C_4$ alkyl group can be for example a methyl, ethyl, n-propyl, n-butyl or 2-methyl propyl radical, preferably methyl or ethyl.

Among the alkanepolycarboxylic acids above, the following acids are particularly retained:

1. phosphonosuccinic acid,
2. 1-phosphono-1,3-propanedicarboxylic acid,
3. 2-phosphono-1,3-propanedicarboxylic acid,
4. 1-phosphono-1,2-propanedicarboxylic acid,
5. 2-phosphono-1,2-propanedicarboxylic acid,
6. 3-phosphono-1,2-propanedicarboxylic acid,
7. 1-phosphono tricarballylic acid,
8. 2-phosphono tricarballylic acid,
9. 1-phosphono-1,2-butanedicarboxylic acid,
10. 2-phosphono-1,2-butanedicarboxylic acid,
11. 3-phosphono-1,2-butanedicarboxylic acid,
12. 4-phosphono-1,2-butanedicarboxylic acid,
13. 1-phosphono-1,3-butanedicarboxylic acid,
14. 2-phosphono-1,3-butanedicarboxylic acid,
15. 3-phosphono-1,3-butanedicarboxylic acid,
16. 4-phosphono-1,3-butanedicarboxylic acid,
17. 1-phosphono-1,4-butanedicarboxylic acid,
18. 2-phosphono-1,4-butanedicarboxylic acid,
19. 2-phosphono-2,3-butanedicarboxylic acid,
20. 1-phosphono-1,2,3-butanetricarboxylic acid,
21. 2-phosphono-1,2,3-butanetricarboxylic acid,
22. 3-phosphono-1,2,3-butanetricarboxylic acid,
23. 4-phosphono-1,2,3-butanetricarboxylic acid,
24. 1-phosphono-1,2,4-butanetricarboxylic acid,
25. 2-phosphono-1,2,4-butanetricarboxylic acid,
26. 3-phosphono-1,2,4-butanetricarboxylic acid,
27. 4-phosphono-1,2,4-butanetricarboxylic acid,
28. 1-phosphono-1,2,3,4-butanetetracarboxylic acid,
29. 2-phosphono-1,2,3,4-butanetetracarboxylic acid,
30. ethoxyhydroxyphosphorylsuccinic acid.

Among the acids according to the present invention, the following acids can notably be used:
- phosphonosuccinic acid,
- a phosphonotricarballylic acid,
- a phosphonopropanedicarboxylic acid,
- a phosphonopropanetricarboxylic acid,
- a phosphonobutanedicarboxylic acid,
- a phosphonobutanetricarboxylic acid,
- a phosphonobutanetetracarboxylic acid,
- 1-phosphono-1,3-propanedicarboxylic acid,
- a 1,2,4-phosphonobutanetricarboxylic acid,
- 2-phosphono-1,2,3,4-butanetetracarboxylic acid,
- ethoxyhydroxyphosphoryl succinic acid.

The alkanepolycarboxylic acids which are usable according to the present invention are described generally and they can be obtained from commercial products by known processes such as those mentioned for example in "HOUBEN-WEYL, Methoden Der Organischen Chemie, Volume 12, tome I, pages 348–350, Goerg Thieme Verlag, Stuttgart, 1963 and in the supplement E2 pages 300–486". The majority of these acids are prepared by acid hydrolysis of the corresponding polyester obtained most often by the Michael reaction of triethylphosphite on the corresponding ethyl alkenepolycarboxylate. The alkanepolycarboxylic acids corresponding to formula I, subsequently designated products of the invention, show useful properties which can be applied in the finishing of cellulose fabrics, notably to impart crease-resistance to them. They are suitable for woven or nonwoven cellulose fabrics, containing 100% cellulose product such as, for example, cotton, as well as for mixtures, for example, polyester-cotton or polyester-rayon. Such mixtures preferably contain, although it is not obligatory, at least 20% cellulose. Whites can be treated effectively with the products according to the invention, as well as colours (printed, dyed, yarn dyed, "cross-dyed" and similar). Substances containing fibers with free hydroxyl groups can also be treated.

The use of the product according to the invention with the substance to be treated generally takes place, although not obligatorily, in the presence of a catalyst. The following acids are notably suitable: hydrochloric, sulphuric, fluoroboric, phosphoric, phosphorous, hypophosphorous, glycolic, maleic, lactic, citric, tartaric and oxalic; metallic salts such as magnesium or zinc chloride, nitrate, fluoroborate or fluorosilicate, ammonium chloride, zirconium oxychloride, sodium or potassium bisulphate, sodium or potassium phosphite or hypophosphite, sodium or potassium dihydrogenophosphate disodium or dipotassium hydrogenophosphate, amine hydrochlorides, such as 2-amino-2-methyl-propanol hydrochloride and similar products, as well as their mixtures.

When a catalyst is used, the quantity employed generally represents between 0.01 and 10%, preferably between 0.05 and 5%, of the weight of the impregnating bath.

The products according to the invention can be applied to textile material using any known and appropriate process, for example by immersion or impregnation. Standard additives such as wetting agents, lubricants, plasticizers, bulking agents, waterproofing products, flame retardants, antisoiling agents, mould inhibitors, fluorescent colouring agents and similar can be incorporated in suitable quantities in these treatment baths. However, these additional products must not interfere with the correct functioning of the products according to the invention, they must not themselves exercise a harmful effect on the material to be treated and it is desirable that they do not contain formaldehyde.

The quantity of product to be applied on the textile substance depends on the nature of this substance and the end result being sought. Generally, it is of the order of 0.5 to 10%, preferably comprised between 2 and 5%, relative to the weight of textile.

During the treatment process of textiles with the products according to the invention, the textile is, for example, impregnated with an aqueous solution of the products of the invention optionally containing the chosen cross-linking catalyst, then the textile which has been impregnated in this way is dried and then subjected to a standard heat treatment in order to achieve cross-linking. Usually this heat treatment is carried out at a temperature greater than 125° C., advantageously at a temperature greater than 150° C.

The drying and cross-linking stages can be consecutive or simultaneous. Optionally, the textile substance can be finished by standard post cross-linking (also called deferred or retarded cross-linking).

Some of the acids which can be used according to the invention are new products. In that case they can be prepared as follows:

Acid 10 can be obtained by acid hydrolysis of the condensation product of an alkyl halide, notably ethyl iodide, on diethyl diethoxyphosphorylsuccinate. Similarly acid 15 can be obtained by acid hydrolysis of the condensation product of methyl iodide on dimethyl 2-dimethoxyphosphoryl glutarate. Acid 9 can be obtained by the condensation of ethyl alphabromobutyrate with ethyl diethylphosphorylacetate followed by acid hydrolysis.

Acid 27 can be prepared by acid hydrolysis of the condensation product of triethyl phosphite with 1,2,4-ethyl 2-butene tricarboxylate. By condensing ethyl diethoxyphosphorylacetate with diethyl mesaconate then by hydrolysing the ester obtained, acid 20 can be obtained. Acid 28 can be obtained by acid hydrolysis of the condensation product of ethyl diethoxyphosphorylacetate with ethyl alphabromotricarballylate. Acid 12 can be obtained by acid hydrolysis of the condensation product of methyl bromoacetate with methyl dimethoxy-4-phosphoryl butanoate. Regarding acid 14, it can be prepared by acid hydrolysis of the condensation product of methyl iodide with dimethyl 3-dimethoxyphosphoryl glutarate.

The mono(alkoxyhydroxyphosphoryl)alkanepolycarboxylic acids according to the invention can be prepared by careful hydrolysis of corresponding alkyl mono(dialkoxyphosphoryl)alkanepolycarboxylates. In fact, it is known that the acid hydrolysis of a mono(alkoxyhydroxyphosphoryl)alkanepolycarboxylic acid into a corresponding monophosphonoalkanepolycarboxylic acid requires much more drastic conditions than those used for the conversion of an alkyl mono(dialkoxyphosphoryl)alkanepolycarboxylate into a mono(alkoxyhydroxyphosphoryl)alkanepolycarboxylic acid (cf. for example, the acid hydrolysis of ethyl diethoxyphosphorylacetate into ethoxyhydroxyphosphorylacetic acid, P. Nylen, Ber., 59, 1119-1128 (1926)). Examples of such preparations are shown hereafter in the experimental part. Therefore a subject of the present invention is also the derivatives corresponding to formula I:

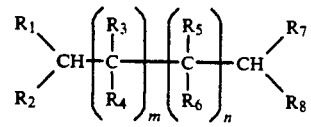

in which $m=1$, $n=1$, $R_2$, $R_4$, $R_6$ and $R_8$ represent a hydrogen atom or a -PO(OH)(OR) group where R represents a hydrogen atom or a $C_1$-$C_4$ alkyl group, $R_1$ represents a carboxyl group and:

either, $R_2$ represents a $PO_3H_2$ group, $R_3$ a COOH group and $R_4$, $R_5$, $R_6$, $R_7$ and $R_8$ represent a hydrogen atom, or, $R_3$ represents a COOH group, $R_4$ a $PO_3H_2$ group and $R_2$, $R_5$, $R_6$, $R_7$ and $R_8$ represent a hydrogen atom, or, $R_3$ represents a COOH group, $R_8$ a $PO_3H_2$ group and $R_2$, $R_4$, $R_5$ $R_6$ and $R_7$ represent a hydrogen atom, or, $R_5$ represents a COOH group, $R_4$ a $PO_3H_2$ group and $R_2$, $R_3$, $R_6$, $R_7$ and $R_8$ represent a hydrogen atom, or, $R_5$ represents a COOH group, $R_6$ a $PO_3H_2$ group and $R_2$, $R_3$, $R_4$, $R_7$ and $R_8$ represent a hydrogen atom, or, $R_3$ and $R_5$ represent a COOH group, $R_2$ a $PO_3H_2$ group and $R_4$, $R_6$, $R_7$ and $R_8$ represent a hydrogen atom, or, $R_3$ and $R_7$ represent a COOH group, $R_8$ a $PO_3H_2$ group and $R_2$, $R_4$, $R_5$ and $R_6$ represent a hydrogen atom, or, $R_3$, $R_5$ and $R_7$ represent a COOH group, $R_2$ a $PO_3H_2$ group and $R_4$, $R_6$, and $R_8$ represent a hydrogen atom.

Also a subject of the present invention is textile finishes characterized in that they contain as active ingredient an alkanepolycarboxylic acid derivative corresponding to formula I.

In the preferred conditions, the finishes described above are characterized in that they contain another catalyst, this can be chosen from the alkali metal salts of hypophosphorous, phosphorous or phosphoric acids. Also finishes are preferred characterized in that they do not contain a catalyst.

The following examples are given for information only; they allow a better understanding of the invention but they do not limit its scope. Except where indicated otherwise, the parts and percentages are given by weight. The crease recovery test is carried out according to the AATCC 66-1972 standard on samples as they are and on samples subjected to three domestic washes at 60° C.; the crease recovery is expressed as the sum of the crease recovery angles obtained in the direction of the warp and in the direction of the weft. The traction resistance of the samples is expressed in daN in the direction of the warp plus in the direction of the weft and is carried out according to the AFNOR G 07.001 standard. The yellowing of fabrics, carried out on a FIXOTEST apparatus at 200° C. for 30 seconds, and the whiteness, expressed in degrees Berger, are measured with a spectrophotometer. The proportion of residual formaldehyde on the fabric determined according to the method described in the Japanese law 112-1973 is equal to zero for all examples.

EXAMPLE 1

0.7 g (13 mmoles) of sodium methylate in stick form is slowly introduced under agitation into a mixture of 79.07 g (0.5 mole) of dimethyl itaconate and 55 g (0.5 mole) of dimethylphosphite while maintaining the temperature of the mixture at 10°+2° C. Then, when the exothermic reaction is finished, the reaction medium is left for 16 hours at ambient temperature, then it is neutralized with concentrated sulphuric acid and finally it is subjected to distillation under reduced pressure at 0.3 mbar. In this way 112 g of 1-2-dimethyl 3-dimethoxyphosphoryl-propanedicarboxylate is isolated distilling at 150° under 0.3 mbar. This ester is immediatly hydrolyzed into 3-phosphono-1-2-propanedicarboxylic acid according to a process similar to that described in Example 3.

EXAMPLE 2

5 g (93 mmoles) of sodium methylate is introduced over 30 minutes under agitation into a mixture of 491.7 g (2.7 moles) of methyl dimethoxyphosphorylacetate and 292.3 g (1.85 moles) of dimethyl itaconate, allowing the exothermic reaction to develop until a temperature of 60° C. is reached. The reaction medium is then left for 22 hours under agitation at 60° C. before being neutralized at ambient temperature with concentrated sulphuric acid, then it is filtered to eliminate the insoluble mineral salts, and finally it is subjected to distillation under reduced pressure. In this way 470 g of 1,2,4-dimethyl 4-diethoxyphosphoryl butanetricarboxylate is isolated, distilling at 180° C. under 0.2 mbar.

EXAMPLE 3

381.1 g (1.12 mole) of 1,2,4-trimethyl 4-dimethoxyphosphoryl butanetricarboxylate prepared in Example 2 is heated for 1 hour at 130° C. with 3.3 g (34 mmoles) of concentrated sulphuric acid and 69 g (1.5 mole) of formic acid. The ethyl formate formed is then eliminated by distillation while introducing 400 g of formic acid into the reaction medium over 22 hours. When no more ethyl formate is collected, the reaction medium is cooled down to ambient temperature, the desired acid crystallizes spontaneously. The crystals are isolated by filtration and recrystallized from hot then cold formic acid. In this way 176.5 g (0.65 mole) of crystallized 4-phosphono 1,2,4-butanetricarboxylic acid is isolated having a melting point of 182° C.

EXAMPLES 4-29

A 100% cotton poplin fabric, scalded and bleached, weighing about 130 g per square meter with a wring-out rate of 75% in an aqueous bath the pH of which has been adjusted with soda to the value indicated in Tables I, II and III containing in solution quantities of acid and optionally quantities of catalyst mentioned in these tables, as well as 2 g per liter of ethoxylated nonylphenol with 10 moles of ethylene oxide, is impregnated in a padding machine. The fabric is then dried for 45 seconds at 120° C., then it is subjected to a heat treatment of 90 seconds at 180° C. on a laboratory stenter.

Then the following are determined on samples of the treated fabric:
the crease recovery on samples as they are and on samples subjected to three domestic washes at 60° C.,
the resistance to traction designated Rt,
the whiteness,
the yellowing, The results obtained are given in Tables I, II and III. It is noted that the products according to the present invention considerably improve the crease recovery properties of the treated fabrics even after washing, without lowering their resistance to traction too much.

The new acid derivatives of formula I can be prepared by hydrolysis, preferably an acid hydrolysis, of a corresponding ester to obtain the desired acid.

NOTES RELATING TO TABLES I, II AND III

The abbreviations used in these tables have the following meaning:
Qty: quantity of product dissolved in the impregnation bath, expressed in grams per liter.
A: succinic acid.
B: tricarballylic acid, commercial product.
C: 1,2,3,4-butanetetracarboxylic acid, commercial product.
$C_1$: anhydrous sodium hypophosphite.
$C_2$: crystallized disodium hydrogenophosphate with 12 water molecules.
Rt: resistance to traction.
$B_1$: whiteness expressed in degree Berger.
Ye: yellowing.

TABLE I

| EXAMPLES | Acid nature | Qty | Catalyst nature | Qty | pH of bath | Crease recovery as is | after 3 washes | Rt | Bl. | Ye |
|---|---|---|---|---|---|---|---|---|---|---|
| 4 | A | 40 |  | 0 | 2.3 | 198 | 189.5 | 60 | 65.5 | 50.8 |
| 5 | A | 40 | $C_1$ | 30 | 2.3 | 219 | 199.7 | 80 | 75 | 66.6 |
| 6 | 1 | 68 |  | 0 | 2.3 | 254.7 | 218.2 | 64 | 67.7 | 54.4 |

TABLE I-continued

| EXAMPLES | Acid nature | Acid Qty | Catalyst nature | Catalyst Qty | pH of bath | Crease recovery as is | Crease recovery after 3 washes | Rt | Bl. | Ye |
|---|---|---|---|---|---|---|---|---|---|---|
| 7  | 1  | 68 | C$_1$ | 30 | 2.3 | 262.5 | 238   | 64    | 75.1 | 64.1 |
| 8  | 1  | 68 | C$_2$ | 30 | 2.3 | 259.2 | 234   | 53    | 64.9 | 38.6 |
| 9  | 2  | 72 |       | 0  | 2.3 | 213.5 | 209   | 55    | 51.6 | 33.6 |
| 10 | 2  | 72 | C$_1$ | 30 | 2.4 | 258   | 226   | 84.2  | 74.4 | 64.1 |
| 11 | 30 | 77 |       | 0  | 2.5 | 244   | 228   | 75.3  | 69.2 | 60.0 |
| 12 | 30 | 77 | C$_1$ | 30 | 2.5 | 252   | 225.5 | 74.3  | 75.3 | 69.7 |
| 13 | 0  | 0  |       | 0  |     | 188   | 183.5 | 116.4 | 78   | 76   |

TABLE II

| EXAMPLES | Acid nature | Acid Qty | Catalyst nature | Catalyst Qty | pH of bath | Crease recovery as is | Crease recovery after 3 washes | Rt | Bl. | Ye |
|---|---|---|---|---|---|---|---|---|---|---|
| 14 | B  | 40   |       | 0  | 2.2 | 194.5 | 203   | 58.7  | 63.8 | 57.1 |
| 15 | B  | 40   | C$_1$ | 30 | 2.4 | 275   | 247   | 67    | 73.2 | 66.4 |
| 16 | 7  | 58.5 |       | 0  | 2.3 | 253   | 245.7 | 62.3  | 71.3 | 61.3 |
| 17 | 7  | 58.5 | C$_1$ | 30 | 2.3 | 271   | 246   | 66    | 75   | 69.2 |
| 18 | 8  | 58.5 |       | 0  | 2.3 | 258   | 241   | 64    | 66.6 | 51   |
| 19 | 8  | 58.5 | C$_1$ | 30 | 2.3 | 282.2 | 250.7 | 63.3  | 72.8 | 64.4 |
| 20 | 25 | 62   |       | 0  | 2.9 | 246   | 221   | 78.1  | 72.5 | 67   |
| 21 | 25 | 62   | C$_1$ | 30 | 2.5 | 259.3 | 232.5 | 70.7  | 75.1 | 71.3 |
| 22 | 27 | 62   |       | 0  | 2.3 | 214.2 | 218.7 | 69.1  | 63.2 | 48.8 |
| 23 | 27 | 62   | C$_1$ | 12 | 2.3 | 246.5 | 225.8 | 68.7  | 73.3 | 65.2 |
| 24 | 27 | 62   | C$_1$ | 30 | 2.3 | 244.5 | 239   | 70.6  | 74.6 | 68.3 |
| 28 |    | 0    |       | 0  |     | 166.2 | 186.7 | 118.1 | 76.8 | 74.4 |

TABLE III

| EXAMPLES | Acid nature | Acid Qty | Catalyst nature | Catalyst Qty | pH of bath | Crease recovery as is | Crease recovery after 3 washes | Rt | Bl. | Ye |
|---|---|---|---|---|---|---|---|---|---|---|
| 25 | c  | 40   | C$_1$ | 30 | 2.3 | 269.5 | 257.5 | 64.3  | 74.3 | 70.6 |
| 26 | 29 | 53.5 |       | 0  | 2.3 | 235.7 | 212.5 | 62.3  | 70.7 | 60.5 |
| 27 | 29 | 53.5 | C$_1$ | 30 | 2.3 | 257.5 | 235.5 | 65    | 75.2 | 68.8 |
| 28 |    | 0    |       | 0  |     | 166.2 | 186.7 | 118.1 | 76.8 | 74.4 |

We claim:

1. A method of cross-linking cellulose with a cross-linking agent, which comprises treating, under suitable conditions, said cellulose with a cross-linking agent the improvement wherein corresponding to the general formula I:

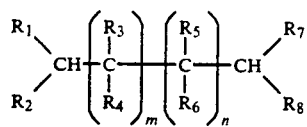

in which:
n and m, identical or different, are and equal to 0 or 1,
R$_1$, R$_3$, R$_5$ and R$_7$ represent a hydrogen atom or a carboxyl group, wherein at least two substituents from said substituents R$_1$, R$_3$, R$_5$ and R$_7$ represent a carboxyl group, and
- one and only one of R$_2$, R$_4$, R$_6$ and R$_8$ represents a -PO(OH)(OR) group where R is a hydrogen atom or C$_1$-C$_4$ alkyl group, and the others of said R$_2$, R$_4$, R$_6$ and R$_8$ each represents a hydrogen atom.

2. A method according to claim 1, characterized in that the derivative of formula I is phosphonosuccinic acid.

3. A method according to claim 1, characterized in that the derivative of formula I is a phosphonotricarballylic acid.

4. A method according to claim 1, characterized in that the derivative of formula I is a phosphonopropanedicarboxylic acid.

5. A method according to claim 1, characterized in that the derivative of formula I is a phosphonopropanetricarboxylic acid.

6. A method according to claim 1, characterized in that the derivative of formula I is a phosphonobutanedicarboxylic acid.

7. A method according to claim 1, characterized in that the derivative of formula I is a phosphonobutanetricarboxylic acid.

8. A method according to claim 1, characterized in that the derivative of formula I is a phosphonobutanetetracarboxylic acid.

9. A method according to claim 1, characterized in that the derivative of formula I is 1-phosphono 1,3-propanedicarboxylic acid.

10. A method according to claim 1, characterized in that the derivative of formula I is 1,2,4-phosphonobutanetricarboxylic acid.

11. A method according to claim 1, characterized in that the derivative of formula I is 2-phosphono 1,2,3,4-butanetetracarboxylic acid.

12. A method according to claim 1, characterized in that the derivative of formula I is ethoxyhydroxyphosphoryl succinic acid.

13. A method according to claim 1, further comprising, impregnating fibrous cellulosic material with an aqueous solution comprising a cross-linking agent of Formula I and heating the impregnated fibrous cellulosic material to produce esterification and cross-linking of the cellulose with said agent of Formula I.

14. A method according to claim 1, further comprising adding a curing catalyst prior to cross-linking with an agent of formula I.

15. A method according to claim 1, wherein said cross-linking occurs in the absence of a curing catalyst.

16. Textile finishes comprising cellulose cross-linked with a derivative of alkanepolycarboxylic acid corresponding to formula I:

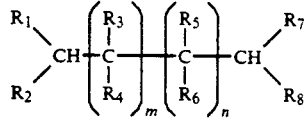

in which:

n and m, identical or different, are equal to 0 or 1, $R_1$, $R_3$, $R_5$ and $R_7$ represent a hydrogen atom or a carboxyl group, it being understood that at least two of the substituents from the said substituents $R_1$, $R_3$, $R_5$ and $R_7$ represent a carboxyl group, $R_2$, $R_4$, $R_6$ and $R_8$ represent a hydrogen atom or a -PO(OH)(OR) group where R is a hydrogen atom or a $C_1$-$C_4$ alkyl group, it being understood that only one substituent from the said substituents $R_2$, $R_4$, $R_6$ and $R_8$ represents said -PO(OH)(OR) group.

17. Finishes according to claim 14, characterized in that in addition they contain a catalyst.

18. Finishes according to claim 15, characterized in that the catalyst is chosen from the alkali metal salts of hypophosphorous, phosphorous or hypophosphoric acids.

19. Finishes according to claim 14, characterized in that they do not contain a catalyst.

* * * * *